United States Patent [19]

Johnson

[11] 4,355,640
[45] Oct. 26, 1982

[54] HYGIENIC DISPENSER

[76] Inventor: Robert C. Johnson, c/o L. Newfield, 2210 Wilshire Blvd. #372, Santa Monica, Calif. 90403

[21] Appl. No.: 149,495

[22] Filed: May 13, 1980

[51] Int. Cl.³ .............................................. A61M 3/00
[52] U.S. Cl. .................................... 128/227; 222/368
[58] Field of Search .............. 128/229, 227, 230, 224, 128/251; 222/368

[56] References Cited

U.S. PATENT DOCUMENTS

| 1,752,698 | 4/1930 | Rogers et al. | 128/227 |
| 1,811,345 | 6/1931 | Bell | 128/227 |
| 2,518,520 | 8/1950 | Broun | 222/368 |
| 2,522,122 | 9/1950 | Kertesz | 128/229 |
| 2,891,543 | 6/1959 | Bidlingmayer et al. | 128/227 X |
| 2,898,011 | 8/1959 | Benton | 222/368 |
| 3,572,338 | 3/1971 | Murray, Jr. | 128/230 |
| 4,000,742 | 1/1977 | DiGiacomo | 128/229 |

Primary Examiner—John D. Yasko
Attorney, Agent, or Firm—Erik M. Arnhem

[57] ABSTRACT

A hygienic dispenser cabinet containing a liquid holding space, and an outlet therefrom, a cylinder there above for holding non-liquid matter, being invertibly mounted therein, to cause the non-liquid matter to drop into and mix with the liquid in the liquid holding space, and a hose connected to the outlet of the cabinet, for dispensing of the solution of liquid and non-liquid matter to parts of a living body.

6 Claims, 4 Drawing Figures

HYGIENIC DISPENSER

FIELD OF THE INVENTION (1) Background of the Invention

The present invention is a dispensing hygienic device, applicable to vaginal douches but may also be used for other medical purposes, such as enemas, rinsing and treatment of burns, wounds, etc.

Our modern society is spoiled with a multitude of appliances and gadgets, but surprisingly enough, homes, especially of young families, lack an appliance that meets the present standard and convenience of feminine hygiene. The device, according to my invention constitutes a self-contained unit, incorporating a tank for a liquid, such as water, a measuring cup mounted invertibly above the tank, fillable with douching powder, which is miscible with the water for obtaining a douching solution; and dispensing means for applying same to the vaginal tract.

(2) Description of the Prior Art

A preliminary patentability search in class 128, subclasses 224, 227, 228, 248 and 251 resulted in finding the following United States Patents:

| | | |
|---|---|---|
| #1.546016 | Eisele | 1925 |
| #1.680.762 | Butler et al | 1928 |
| #2.062.040 | Rigney | 1936 |
| #2.339.908 | Brewer et al | 1944 |
| #2.585.198 | Warren | 1952 |
| #2.650.739 | Boydstun | 1953 |
| #2.891.543 | Bidlingmayer et al | 1959 |
| #3.667.467 | Dory | 1972 |
| #4.061.144 | Strickman et al | 1977 |

None of the above enumerated patents appears to disclose the structure of my invention.

Strickman refers to a disposable douche bag, including a powder containing membrane openable by tearing and a syringe. Dory describes a douche bag containing ornamental portable support. Warren and Boydstun refer to devices for dispensing granulated matter, incorporating inverting means. The rest of the cited patents are included as being of general interest.

SUMMARY OF THE INVENTION

In addition to what has been stated above, the hygienic device serves a number of useful purposes, and comprises an elegantly executed cabinet for discreetly hanging, e.g., on a bathroom wall; the interior of the device is easily accessible by way of a pivotable lid and houses a minimum of strictly functional and detachable or movable components, thus facilitating cleaning, etc., of the latter; the lower part of the device constitutes a tank for water; and upper interior portion of the device is demarcated by narrow ledges upon which a removable funnel with a base rests, the latter having an opening through which water may be poured into the tank. Below the based funnel is provided a solid rotary cylinder having a centered cavity constituting a measuring cup, which may be aligned with the outlet of the funnel; douche powder, for example, is then poured through the funnel into the measuring cup. The tank may be pre-filled with water, or water having an appropriate temperature may be poured into the tank for immediate application. Different types of powder, as required, may then be poured into the measuring cup, which when inverted causes the powder to drop into and mix with the water, producing a solution, ready to be applied by way of exterior dispensing means; the latter, when not in use, may be concealed at one side of the device, presenting an overall appearance of an attractive compact cabinet.

Thus, it is an object of the invention to provide a self-contained device for douching or general medical applications.

It is another object of the invention to provide a hygienic device including means for holding liquid and measured powder separately but miscible with one another when required for such medical application.

It is still a further object to provide a hygienic device consisting of a minimum of tastefully accommodated components, being relatively inexpensive to manufacture.

DESCRIPTION OF THE PREFERRED EMBODIMENT OF THE INVENTION

Figure 1:
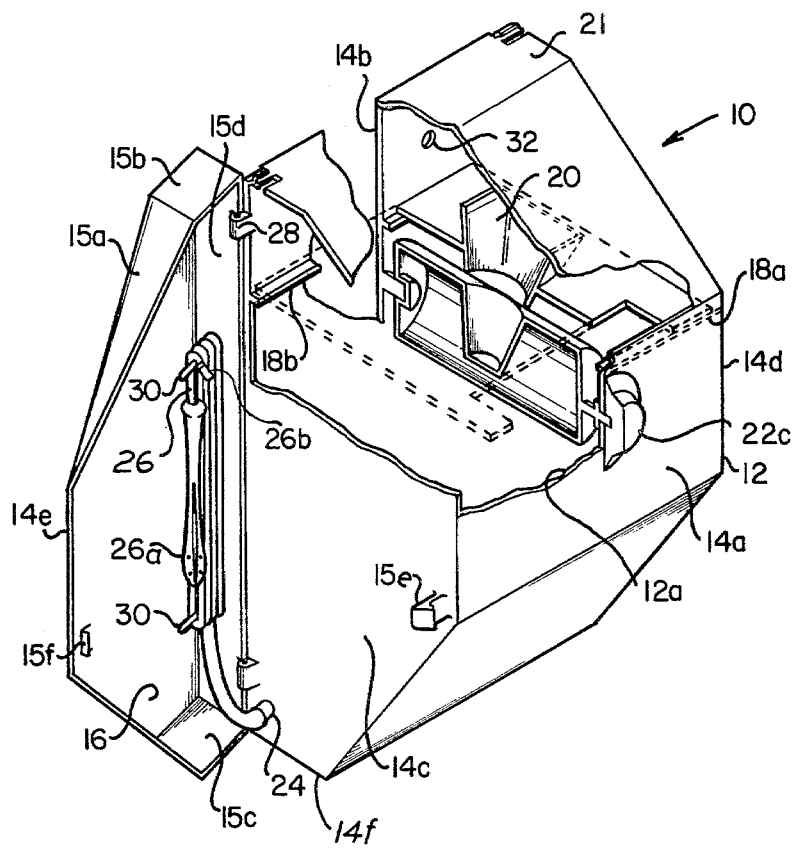
FIG. 1 is a broken away perspective view of a hygienic device showing interior movable components thereof in section.

In the drawings like reference characters designate similar parts in the different views.

Referring now in detail to FIG. 1 of the drawings, numeral 10 designates the hygienic device in its entirety.

Figure 2:
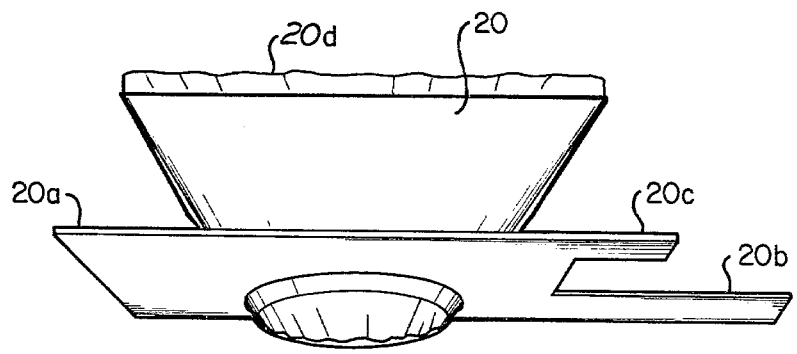
FIG. 2 is a perspective view of a based funnel, detachably mountable in the device.
Figure 3:
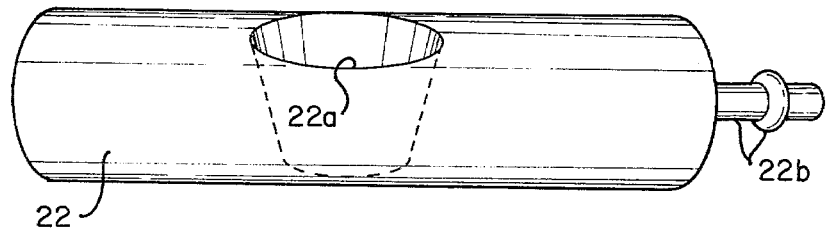
FIG. 3 is a perspective view of a cylinder with a centered measuring cavity, rotatably mounted in the device beneath the funnel of FIG. 2.
Figure 4:
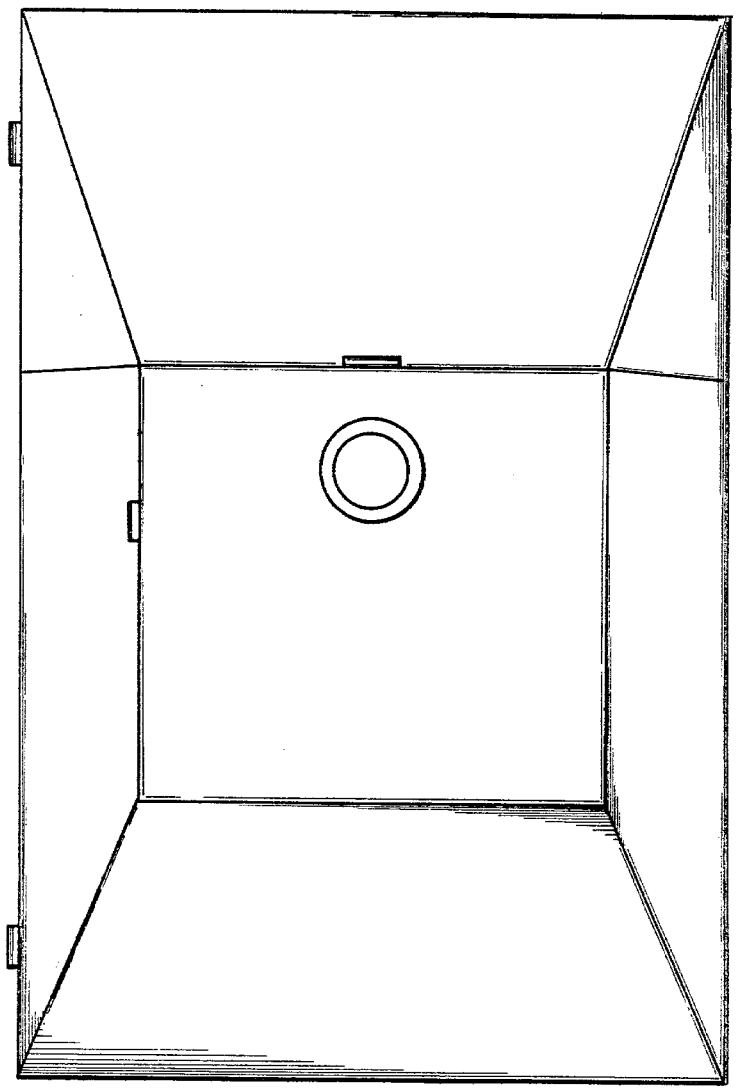
FIG. 4 is a front view in elevation of the hygienic device of FIG. 1.

All the components of the device are or may be accommodated within the confines of housing means, e.g., a cabinet 12, having a front, rear, lateral and bottom wall surfaces 14a, b, c, d, e and f respectively, of which a lateral surface 14e constitutes concealing means, e.g., a hinged member 16, mounted pivotably adjacent lateral surface 14c, for purposes which will be explained further on. Supporting means, e.g., ledges 18a, b extend, respectively along the interior front and rear surfaces of an upper portion of walls 14a, b, (a section of which is shown in FIG. 1), serving as support for channeling means, e.g., a based funnel 20; base 20a encompasses funnel 20 and having substantially rectangular shape with two unevenly projecting members 20b, c projecting horizontally and parallely from one side (as illustrated in FIG. 2) of base 20a. Based funnel 20 is detachably accommodated with its edges resting on ledges 18a, b within the device 10; its base will, thus constitute an upper floor of the device having a cut-out opening (formed by the arms 20b, c) through which a liquid, e.g., water may be poured into a space, e.g., tank 12a, forming the lower portion of cabinet 12. Invertible means, e.g., a substantially solid cylinder 22 is mounted rotatably beneath and in alignment with based funnel 20. A centered portion of cylinder 22 is provided with a cavity, serving as a measuring cup 22a (for e.g., douche powder) the outlines of which are indicated by dotted lines (FIG. 3); cylinder 22 extends along the entire width of cabinet 12 and is rotatably but frictionally mounted to front and rear wall surfaces 14a, b of device 10, by means of e.g., projecting rods and retaining rings 22b, one pair of which is shown in FIG. 3, or by any other appropriate means. Cylnder 22 with measuring cup 22a is turned by actuating a knob 22c connected to rod 22b at the outside of wall 14a, through which rod 22b extends.

At least a portion of the outlet opening of funnel 20 protrudes somewhat below the funnel base 20a, as shown on FIG. 2 so that, when funnel 20 is placed within the device on ledges 18 and the measuring cavity 22a is aligned with the outlet opening of funnel 20, the downwardly extending protrusion of the latter will project into cavity 20a and stabilize the rotary cylinder while powder is poured through funnel 20 into cavity 22a.

In addition to applying funnel 20, one may also, for sanitary purposes, utilize a disposable paper liner 20d, fittingly insertable in funnel 20.

Closing means, e.g., a lid 21 is hingedly mounted to the upper edge of rear wall surface 14b, for covering of the components within cabinet 12.

When tank 12a of cabinet 12 is filled with water to an appropriate level (which may be indicated, e.g., by markings on the exterior wall of the cabinet), the based funnel 20 removed, and the measuring cup 22, containing powder, inverted by turning knob 22c, the powder will drop into and disperse within the water, producing a ready-to-use douche solution.

An outlet opening 24 for the solution is provided at a lower portion of wall surface 14c and dispensing means, e.g., an appropriately dimensioned hose 26 is connected by any suitable means to outlet opening 24. Hose 26 terminates in a perforated pipe, e.g., vaginal pipe 26a through which the douche solution flows.

A conventional resilient clip 26b which is obtainable commercially at drugstores, etc., may be applied, preferably to a hose portion adjacent pipe 26a and manipulated to either restrict or release the flow of solution through hose 26.

The flat double wall surface 14e, its edges extending angularly into inwardly directed space forming shoulders 15a, b, c, d, the elongated shoulder 15d of which is hingedly connected at 28 to lateral wall 14c, thus constitutes a closable compartment in conjunction with the latter. When hose 26 is not in use, it may be wound around two support means, e.g., pins 30, projecting integrally and spatially from one another on the interior surface of shoulder 15d (FIG. 1).

Wall surface 14e may then be turned inwardly towards wall surface 14c, locked by means of a conventional snap closure (indicated at 15e, f), thus concealing hose 26 with pipe 26a in the compartment formed therebetween.

Cabinet 12 is, ideally hung on a bathroom wall and apertures 32 (one of which is shown in FIG. 1) are provided on rear wall surface 14b for engagement with bolts or screws driven into the bathroom wall.

The pressure of the liquid flowing through hose 26 will depend on the wall elevation of the cabinet from the bathroom floor. For example, if cabinet 12 is hung 5 feet above the bathroom floor, the liquid will flow at a pressure of about 1.9 pounds per square feet. Obviously, the pressure will decrease with lowering of the elevation of the cabinet, and the user may, thus control the pressure and avoid excess intravaginal water pressure.

The following approximate exterior dimensions of cabinet 12 are suggested:

Height: 11"
Length: 6"
Depth: 3¾"

The cabinet is preferably made of a sturdy plastic material.

The operation of the device, according to the invention, is very simple and appears readily from the foregoing description and drawings.

While the foregoing has illustrated and described what is now contemplated to be the best mode of carrying out the invention, the above embodiment thereof is, of course, subject to modification without departing from the spirit and scope of the invention.

Therefore, it is not intended to restrict the invention to the particular constructions illustrated and described but to cover all modifications, that may fall within the scope of the appended claims.

I claim:

1. A dispensing hygienic device, comprising:
   (a) a cabinet having front, rear, lateral, and bottom wall surfaces, respectively, a liquid holding space therewithin, an outlet therefrom and a closable top.
   (b) a cylinder, having a centered cavity for holding a non-liquid matter, mounted invertibly between two opposite wall surfaces of the cabinet, causing, when the cylinder is inverted, non-liquid matter therein to drop into and disperse within liquid in the holding space;
   (c) a knob disposed rotatably exteriorly to the cabinet and connected to the cylinder through a wall surface of the cabinet, facilitating the inversion of the cylinder;
   (d) Dispensing means including a hose, connected to the outlet of the cabinet and terminating in a pipe for dispensing the solution of liquid and non-liquid matters to parts of a living body;
   (e) a resilient clip, applicable to a portion of the hose to restrict or release the flow of solution dispersed therethrough.

2. A dispensing hygienic device, according to claim 1, wherein chanelling means for transferring non-liquid matter to the cavity in the cylinder is detachably mounted there above and in alignment therewith.

3. A dispensing hygienic device, according to claim 2, wherein the chanelling means is a funnel having a base, including projecting members which extend spatially apart from one side of the base, so as to form an opening therein for pouring of liquid into the liquid holding space of the cabinet, the outlet opening of the funnel terminates in a protrusion, extending beneath the base thereof for insertion within the cavity of the cylinder, the edges of the base rest on ledges, which extend along interior wall surfaces of the cabinet above the cavernous cylinder therewithin.

4. A dispensing hygienic device, according to claim 1, wherein a spatial member is mounted openable over one of the wall surfaces thereof, within which the hose and pipe are concealably accommodated.

5. A dispensing hygienic device, according to claim 4, wherein support means project from the interior of the spatial member, around which the hose is wound when not in use.

6. A dispensing hygienic device, according to claim 4, wherein the spatial member comprises a surface having edges extending angularly into inwardly directed space forming shoulders, one of which being hingedly connected to a wall surface of the cabinet and forming a closable compartment therewith.

* * * * *